United States Patent
Itai

(10) Patent No.: US 9,619,938 B2
(45) Date of Patent: Apr. 11, 2017

(54) VIRTUAL ENDOSCOPIC IMAGE DISPLAY APPARATUS, METHOD AND PROGRAM

(71) Applicant: FUJIFILM Corporation, Tokyo (JP)

(72) Inventor: Yoshinori Itai, Tokyo (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 0 days.

(21) Appl. No.: 14/747,027

(22) Filed: Jun. 23, 2015

(65) Prior Publication Data

US 2015/0287243 A1 Oct. 8, 2015

Related U.S. Application Data

(63) Continuation of application No. PCT/JP2013/007402, filed on Dec. 17, 2013.

(30) Foreign Application Priority Data

Dec. 27, 2012 (JP) ................................ 2012-283873

(51) Int. Cl.
G06T 15/00 (2011.01)
G06T 19/00 (2011.01)
(Continued)

(52) U.S. Cl.
CPC ............ *G06T 19/003* (2013.01); *A61B 6/032* (2013.01); *A61B 6/466* (2013.01); *A61B 6/50* (2013.01);
(Continued)

(58) Field of Classification Search
None
See application file for complete search history.

(56) References Cited

U.S. PATENT DOCUMENTS 5,717,848 A 2/1998 Watanabe et al.
6,377,264 B1 4/2002 Iizuka et al.
(Continued)

FOREIGN PATENT DOCUMENTS

JP 4-127279 A 4/1992
JP 2000-126457 A 5/2000
(Continued)

OTHER PUBLICATIONS

Written Opinion, dated Feb. 18, 2014, issued in corresponding International Application No. PCT/JP2013/007402, 7 pages in English and Japanese.
(Continued)

*Primary Examiner* — Frank Chen
(74) *Attorney, Agent, or Firm* — Sughrue Mion, PLLC

(57) ABSTRACT

Specification of a point of interest is received. After then, a distance of movement on a path from an initial viewpoint is obtained based on an operation amount obtained at an operation unit, such as a mouse. View line vectors are set by sequentially changing the view line vectors from an initial view line vector with its start point located at the initial viewpoint to a shortest view line vector connecting a point of interest and a viewpoint at a shortest distance by moving, along the path, a viewpoint of a virtual endoscope on the path from the initial viewpoint closer to the point of interest and by changing the direction of a view line of the virtual endoscope closer to a direction toward the point of interest. Virtual endoscopic images are sequentially generated based on the set view line vectors, and the generated virtual endoscopic images are sequentially displayed.

14 Claims, 5 Drawing Sheets

(51) Int. Cl.
*A61B 6/03* (2006.01)
*A61B 6/00* (2006.01)
*G06F 19/12* (2011.01)
*G06F 19/26* (2011.01)

(52) U.S. Cl.
CPC .............. *G06F 19/12* (2013.01); *G06F 19/26* (2013.01); *G06T 2210/41* (2013.01)

(56) References Cited

U.S. PATENT DOCUMENTS

| | | | |
|---|---|---|---|
| 8,834,245 B2* | 9/2014 | Haigh-Hutchinson | A63F 13/10 463/2 |
| 2002/0075264 A1 | 6/2002 | Iizuka et al. | |
| 2007/0052724 A1* | 3/2007 | Graham | G06T 19/003 345/620 |
| 2009/0063118 A1* | 3/2009 | Dachille | G06F 17/30262 703/11 |
| 2009/0161927 A1 | 6/2009 | Mori et al. | |
| 2010/0033429 A1* | 2/2010 | Olivan Bescos | G06F 3/04815 345/157 |
| 2012/0033866 A1 | 2/2012 | Masumoto et al. | |
| 2014/0329596 A1* | 11/2014 | Omi | A63F 13/00 463/31 |
| 2015/0086181 A1* | 3/2015 | Mariani | G06T 19/003 386/241 |

FOREIGN PATENT DOCUMENTS

| | | |
|---|---|---|
| JP | 2011-206297 A | 10/2011 |
| WO | 2005/002432 A2 | 1/2005 |
| WO | 2007/129493 A1 | 11/2007 |
| WO | 2010/119690 A1 | 10/2010 |

OTHER PUBLICATIONS

Masahiro Yasue et al., "Thinning Algorithms for Three-Dimensional Gray Images and Their Application to Medical Images with Comparative Evaluation of Performance", Journal of the Institute of Electronics, Information and Communication Engineers, 1996, pp. 1664-1674, vol. J79-D-II, No. 10.

Toyofumi Saito et al., "An Improvement of Three Dimensional Thinning Method Using a Skeleton Based on the Euclidean Distance Transformation—A Method to Control Spurious Branches", Journal of the Institute of Electronics, Information and Communication Engineers, 2001, pp. 1628-1635, vol. J84-D-II, No. 8.

Lichan Hong et al., "Virtual Voyage: Interactive Navigation in the Human Colon", Proceedings of the 24th annual conference on Computer graphics and interactive techniques, 1997, pp. 27-34.

International Search Report for PCT/JP2013/007402 dated Febuary 18, 2014.

* cited by examiner

FIG.6
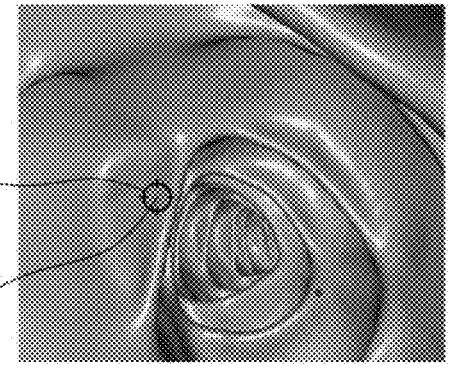
POINT OF INTEREST
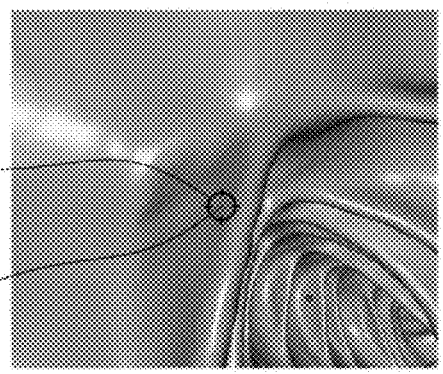
POINT OF INTEREST
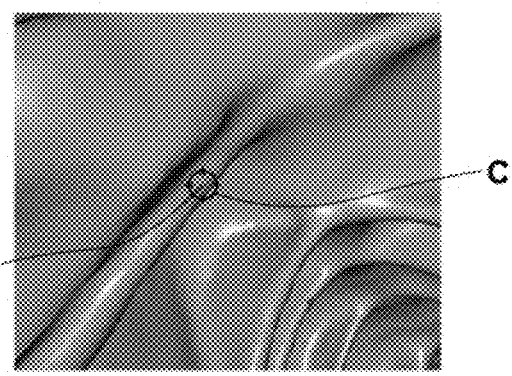
POINT OF INTEREST
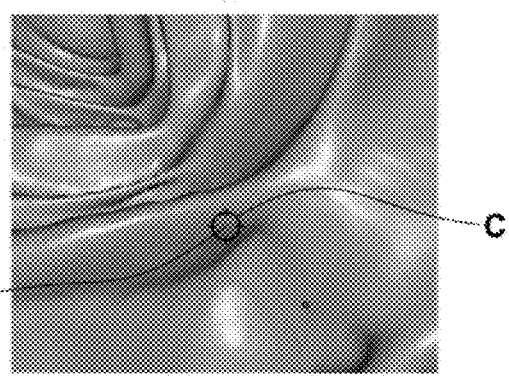
POINT OF INTEREST

VIRTUAL ENDOSCOPIC IMAGE DISPLAY APPARATUS, METHOD AND PROGRAM

CROSS-REFERENCE TO RELATED APPLICATIONS

This application is a Continuation of PCT International Application No. PCT/JP2013/007402 filed on Dec. 17, 2013, which claims priority under 35 U.S.C. §119(a) to Japanese Patent Application No. 2012-283873 filed on Dec. 27, 2012. Each of the above applications is hereby expressly incorporated by reference, in its entirety, into the present application.

BACKGROUND OF THE INVENTION

Field of the Invention

The present invention relates to a virtual endoscopic image display apparatus, method and program that generates, based on a three-dimensional image of a subject to be examined, a virtual endoscopic image by a virtual endoscope, simulating imaging performed by an endoscope, and displays the virtual endoscopic image.

Description of the Related Art

In recent years, a tubular tissue, such as a large intestine, a small intestine, a bronchus and a blood vessel, of a patient is extracted from a three-dimensional image imaged by a modality, such as a CT (Computed Tomography) apparatus, and a three-dimensional image of the extracted tubular tissue is used in diagnosis based on images.

For example, the following technique has been proposed in colonography of the large intestine. A path of an endoscope that passes through the inside of the large intestine region is determined based on a three-dimensional image of the large intestine region. While a viewpoint is moved along the determined path, a virtual endoscopic image resembling an image actually imaged from the viewpoint by the endoscope is generated. A path to a target point is navigated by displaying this virtual endoscopic image.

SUMMARY OF THE INVENTION

Meanwhile, when a suspected lesion region, for example, such as a suspected tumor has been found in the colonography of the large intestine, a user wants to check the lesion region in a virtual endoscopic image in some cases.

In such a case, conventionally, a user needed to set and input the position of a viewpoint of an endoscope supposed to be close to the lesion region and the direction of a view line of the endoscope toward the lesion region, and the operation was troublesome for the user. Further, the direction of the view line set and input by the user was not always directed to the lesion region. When a virtual endoscopic image was generated based on these kinds of operation, the lesion region did not appear at an appropriate position in the generated virtual endoscopic image in some cases, and fine adjustment of the position of the viewpoint and the direction of the view line was needed.

Further, a user wants to observe not only the condition of the proximity of a lesion region but also the condition of a surrounding region of the lesion region in some cases. In such a case, the user needed to additionally set and input the position of a viewpoint and the direction of a view line again, and the operation became more troublesome. Especially, when a suspected lesion region is present on a fold in the large intestine, a user wants to observe not only a virtual endoscopic image viewing the suspected lesion region from one side of the fold, but also a virtual endoscopic image viewing the suspected lesion region from the other side of the fold, in other words, from the back side of the fold in some cases. In such a case, the user also needed to additionally set and input the position of new viewpoints and the direction of new view lines to generate these virtual endoscopic images, and that lowered the efficiency of diagnosis.

Meanwhile, Japanese Unexamined Patent Publication No. 2011-206297 (Patent Document 1) proposes a method for making observation of a point of interest easy by automatically generating a virtual endoscopic image viewing the point of interest from the front of the point of interest when the virtual endoscopic image including the desirable point of interest is generated. However, in the method disclosed in Patent Document 1, observation of the virtual endoscopic image viewing the point of interest only from the front is possible. Observation of a virtual endoscopic image of a surrounding region of the point of interest is not possible. Therefore, a user also needs to set and input the position of a viewpoint and the direction of a view line again to generate such a virtual endoscopic image of the surrounding region of the point of interest.

In view of the foregoing circumstances, it is an object of the present invention to provide a virtual endoscopic image display apparatus, method and program that is able to sequentially generate and display virtual endoscopic images of a surrounding region of a point of interest, such as a lesion region, and also to generate and display a virtual endoscopic image viewing the point of interest from the front, and which is easily observable, only by a simple operation by an operation unit, such as a mouse.

A virtual endoscopic image display apparatus of the present invention includes a virtual endoscopic image generation unit that generates, based on a three-dimensional image of a subject to be examined, a virtual endoscopic image by a virtual endoscope, simulating imaging performed by an endoscope inserted into the subject to be examined and a display control unit that displays the virtual endoscopic image. The virtual endoscopic image display apparatus includes a path setting unit that sets a path of the virtual endoscope in the three-dimensional image of the subject to be examined, a point-of-interest specification receiving unit that receives specification of a point of interest in the virtual endoscopic image, an operation amount obtainment unit that obtains an operation amount received at an operation unit after specification of the point of interest has been received, a movement distance obtainment unit that obtains, based on the operation amount obtained by the operation amount obtainment unit, a distance of movement of the virtual endoscope on the path from an initial viewpoint, and a view line vector setting unit that sets, based on the distance of movement obtained by the movement distance obtainment unit, view line vectors by sequentially changing the view line vectors from an initial view line vector with its start point located at the initial viewpoint to a shortest view line vector connecting a viewpoint on the path at a shortest distance from the point of interest and the point of interest to each other by moving, along the path, a viewpoint of the virtual endoscope on the path from the initial viewpoint closer to the point of interest and by changing the direction of a view line of the virtual endoscope closer to a direction toward the point of interest. Further, the virtual endoscopic image generation unit sequentially generates the virtual endoscopic image based on the view line vector set by the view line vector setting unit, and the display control unit sequentially displays the virtual endoscopic image based on change of the view line vectors.

In the virtual endoscopic image display apparatus of the present invention, the view line vector setting unit may further set a view line vector connecting a viewpoint on the path moved along the path further forward from the viewpoint of the shortest view line vector and the point of interest to each other.

Further, the view line vector setting unit may set a view line vector by changing a viewpoint of a view line vector that is currently set to the initial viewpoint when an operation at the operation unit has ended.

Further, the view line vector setting unit may set view line vectors by sequentially changing viewpoints from the viewpoint of the view line vector that is currently set to the initial viewpoint, and the display control unit may sequentially display the virtual endoscopic image based on change of the view line vectors.

Further, the virtual endoscopic image generation unit may receive an instruction for recording the virtual endoscopic image during operation at the operation unit, and record a virtual endoscopic image generated based on a view line vector that is being set when the instruction for recording has been received.

Further, the view line vector setting unit may sequentially set the view line vectors in such a manner that the direction of a view line gradually becomes closer to a direction toward the point of interest as the viewpoint becomes closer to the point of interest.

Further, the view line vector setting unit may make an amount of change of the view line vector becoming closer to the shortest view line vector larger when a viewpoint is present closer to the viewpoint on the path at the shortest distance from the point of interest than when the viewpoint is present closer to the initial viewpoint.

Further, a notification unit that notifies that the shortest view line vector is being set by the view line vector setting unit may be provided.

Further, a notification unit that notifies that a view line vector that is currently set by the view line vector setting unit is a view line vector including a viewpoint moved on the path further forward from the viewpoint of the shortest view line vector may be provided.

Further, an initial viewpoint specification receiving unit that receives specification of the initial viewpoint in the three-dimensional image may be provided.

Further, the point-of-interest specification receiving unit may include a mouse, and receive specification of the point of interest by receiving specification of the position of a cursor displayed in the virtual endoscopic image and a click operation of the mouse.

Further, the operation unit may include a mouse, and the operation amount obtainment unit may obtain an operation amount of drag operation or wheel operation of the mouse.

A virtual endoscopic image display method of the present invention includes the steps of generating, based on a three-dimensional image of a subject to be examined, a virtual endoscopic image by a virtual endoscope, simulating imaging performed by an endoscope inserted into the subject to be examined, and displaying the generated virtual endoscopic image. The virtual endoscopic image display method includes the steps of setting a path of the virtual endoscope in the three-dimensional image of the subject to be examined, receiving specification of a point of interest in the virtual endoscopic image, obtaining an operation amount received at an operation unit after specification of the point of interest has been received, obtaining, based on the obtained operation amount, a distance of movement of the virtual endoscope on the path from an initial viewpoint, setting, based on the obtained distance of movement, view line vectors by sequentially changing the view line vectors from an initial view line vector with its start point located at the initial viewpoint to a shortest view line vector connecting a viewpoint on the path at a shortest distance from the point of interest and the point of interest to each other by moving, along the path, a viewpoint of the virtual endoscope on the path from the initial viewpoint closer to the point of interest and by changing the direction of a view line of the virtual endoscope closer to a direction toward the point of interest, generating sequentially the virtual endoscopic image based on the set view line vector, and displaying sequentially the generated virtual endoscopic image based on change of the view line vectors.

A virtual endoscopic image display program of the present invention causes a computer to function as a virtual endoscopic image generation unit that generates, based on a three-dimensional image of a subject to be examined, a virtual endoscopic image by a virtual endoscope, simulating imaging performed by an endoscope inserted into the subject to be examined, and a display control unit that displays the virtual endoscopic image. The virtual endoscopic image display program further causes the computer to function as a path setting unit that sets a path of the virtual endoscope in the three-dimensional image of the subject to be examined, a point-of-interest specification receiving unit that receives specification of a point of interest in the virtual endoscopic image, an operation amount obtainment unit that obtains an operation amount received at an operation unit after specification of the point of interest has been received, a movement distance obtainment unit that obtains, based on the operation amount obtained by the operation amount obtainment unit, a distance of movement of the virtual endoscope on the path from an initial viewpoint, and a view line vector setting unit that sets, based on the distance of movement obtained by the movement distance obtainment unit, view line vectors by sequentially changing the view line vectors from an initial view line vector with its start point located at the initial viewpoint to a shortest view line vector connecting a viewpoint on the path at a shortest distance from the point of interest and the point of interest to each other by moving, along the path, a viewpoint of the virtual endoscope on the path from the initial viewpoint closer to the point of interest and by changing the direction of a view line of the virtual endoscope closer to a direction toward the point of interest. Further, the virtual endoscopic image generation unit sequentially generates the virtual endoscopic image based on the view line vector set by the view line vector setting unit, and the display control unit sequentially displays the virtual endoscopic image based on change of the view line vectors.

According to the virtual endoscopic image display apparatus, method and program of the present invention, specification of a point of interest is received. After then, a distance of movement on a path from an initial viewpoint is obtained based on an operation amount received at an operation unit, such as a mouse. Further, view line vectors are set, based on the obtained distance of movement, by sequentially changing the view line vectors from an initial view line vector with its start point located at the initial viewpoint to a shortest view line vector with a viewpoint located at a shortest distance from the point of interest by moving, along the path, a viewpoint of the virtual endoscope on the path from the initial viewpoint closer to the point of interest and by changing the direction of a view line of the virtual endoscope closer to a direction toward the point of interest. Further, virtual endoscopic images are sequentially generated based on the set view line vectors, and the generated virtual endoscopic images are sequentially displayed. Therefore, it is possible to sequentially generate and display virtual endoscopic images of a surrounding region of the point of interest and also to generate and display a virtual endoscopic image based on a shortest view line vector, in other words, a virtual endoscopic image viewing the point of interest from the front, and which is easily observable, only by a simple operation by the operation unit, such as a mouse.

BRIEF DESCRIPTION OF THE DRAWINGS

FIG. 6 is a diagram illustrating an example of virtual endoscopic images sequentially generated based on change of view line vectors.

DESCRIPTION OF THE PREFERRED EMBODIMENTS

Figure 1:
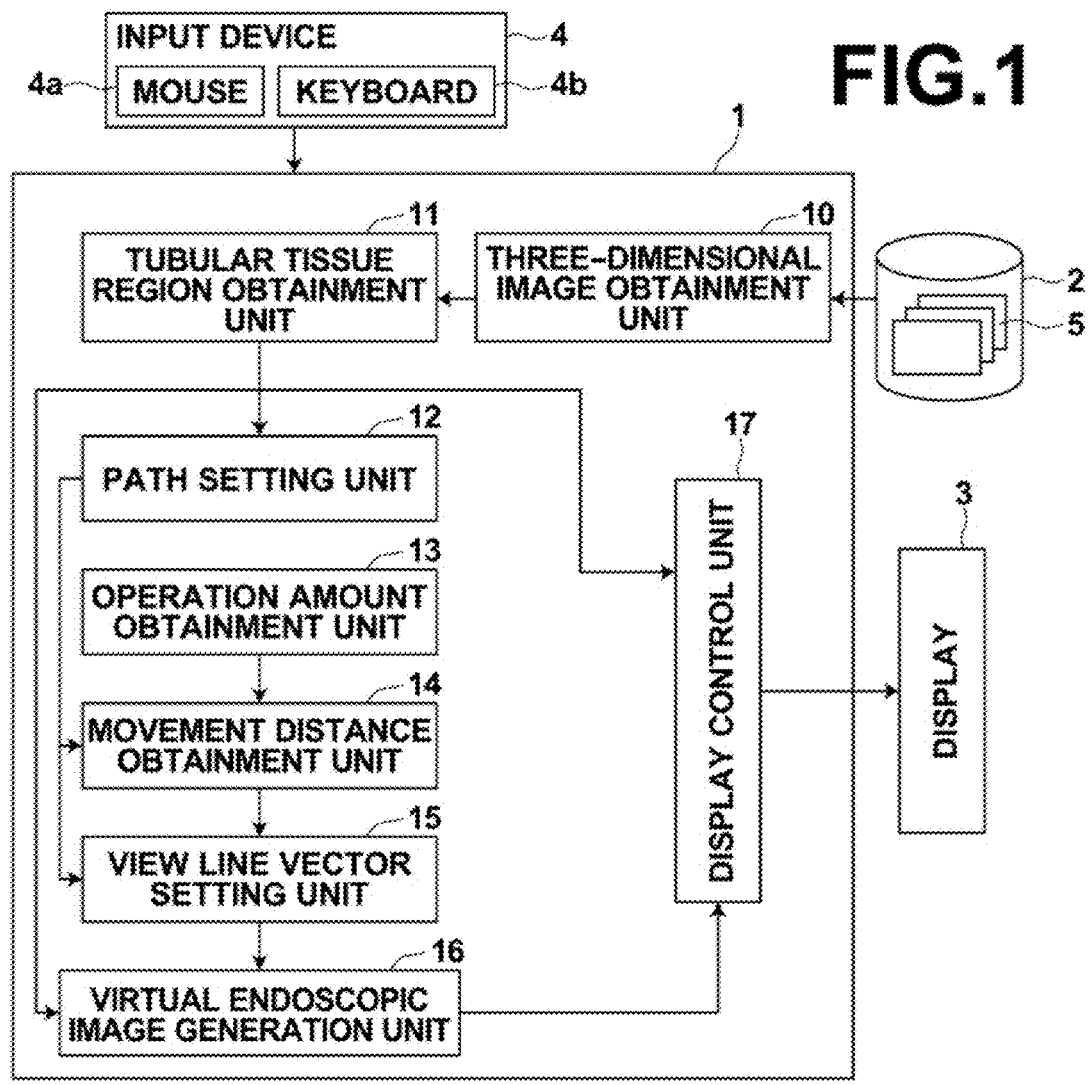
FIG. 1 is a schematic block diagram illustrating the configuration of an endoscopic image diagnosis support system using an embodiment of a virtual endoscopic image display apparatus, method and program of the present invention.
Figure 2:
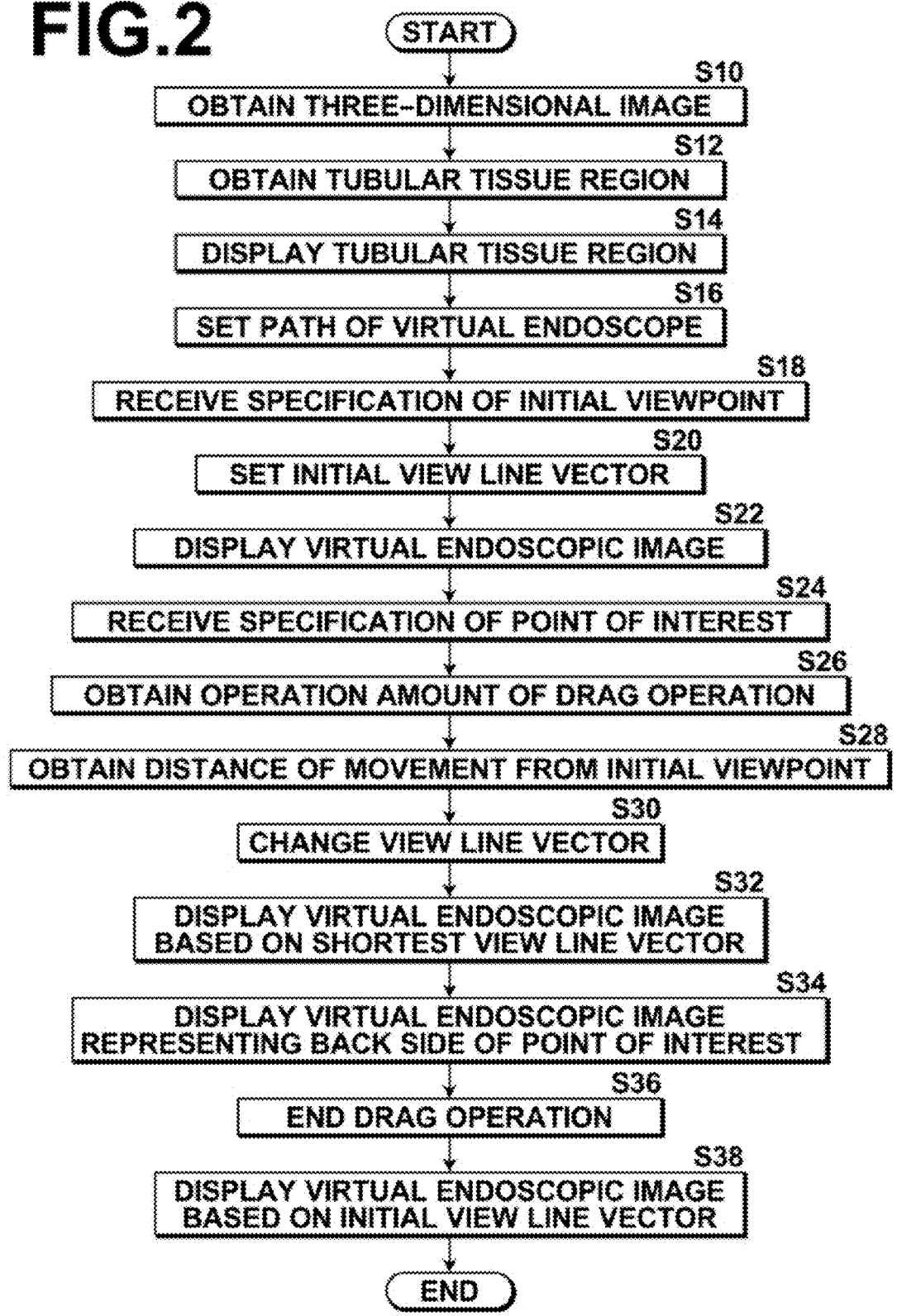
FIG. 2 is a flowchart for explaining the action of the endoscopic image diagnosis support system illustrated in FIG. 1.

Hereinafter, an endoscopic image diagnosis support system using an embodiment of a virtual endoscopic image display apparatus, method and program of the present invention will be described in detail with reference to drawings. FIG. 1 is a schematic block diagram illustrating the configuration of an endoscopic image diagnosis support system according to an embodiment of the present invention.

As illustrated in FIG. 1, the endoscopic image diagnosis support system according to an embodiment of the present invention includes an endoscopic image diagnosis support apparatus 1, a three-dimensional image storage server 2, a display 3 and an input device 4.

The endoscopic image diagnosis support apparatus 1 is a computer in which a virtual endoscopic image display program according to an embodiment of the present invention has been installed.

The endoscopic image diagnosis support apparatus 1 includes a central processing unit (CPU), a semiconductor memory and a storage device, such as a hard disk and an SSD (Solid State Drive), in which the virtual endoscopic image display program according to an embodiment of the present invention has been installed. These kinds of hardware configure a three-dimensional image obtainment unit 10, a tubular tissue region obtainment unit 11, a path setting unit 12, an operation amount obtainment unit 13, a movement distance obtainment unit 14, a view line vector setting unit 15, a virtual endoscopic image generation unit 16, and a display control unit 17, as illustrated in FIG. 1. Further, each of the aforementioned units operates by execution of the virtual endoscopic image display program according to an embodiment of the present invention, which is installed in the hard disk, by the central processing unit.

The three-dimensional image obtainment unit 10 obtains a three-dimensional image 5 of a subject to be examined that has been imaged in advance before surgery or examination that will use an endoscopy apparatus or the like. The three-dimensional image 5 is, for example, volume data reconstructed from slice data output from a CT apparatus, an MRI (Magnetic Resonance Imaging) apparatus or the like, volume data output from an MS (Multi Slice) CT apparatus or a cone beam CT apparatus, and the like. The three-dimensional image 5 is stored in advance in the three-dimensional image storage server 2 together with identification information about a subject to be examined.

The three-dimensional image obtainment unit 10 reads out the three-dimensional image 5 corresponding to identification information about the subject to be examined, which has been input at the input device 4, from the three-dimensional image storage server 2.

The three-dimensional image 5 obtained by the three-dimensional image obtainment unit 10 is input to the tubular tissue region obtainment unit 11. The tubular tissue region obtainment unit 11 obtains a tubular tissue region in the subject to be examined from the input three-dimensional image 5. The tubular tissue is, for example, the large intestine, the small intestine, the bronchi, and blood vessels, such as coronary arteries, but may be other tubular tissues, which are not limited to these tissues. In the embodiment of the present invention, the shape of the large intestine is extracted and obtained.

Specifically, as a method for extracting a large intestine region, first, plural axial cross-sectional images representing cross sections (axial section) perpendicular to a body axis are generated based on a three-dimensional image 5. Then, processing for dividing each of the axial cross-sectional images into a region outside the body and a region inside the body with respect to the surface of the body is performed by using a known technique. For example, binarization processing is performed on an input axial cross-sectional image, and an outline is extracted by outline extraction processing. An inside of the extracted outline is extracted as an internal region of the body (human body). Next, binarization processing is performed on an axial cross-sectional image of the internal region of the body by using a threshold, and a candidate of a large intestine region is extracted from each axial cross-sectional image. Specifically, air is present in the tube of the large intestine. Therefore, binarization processing is performed by setting a threshold corresponding to the CT value of air (for example, −600 or less), and an air region in the body in each axial cross-sectional image is extracted as a candidate of the large intestine region. Finally, the large intestine region is obtained by extracting only parts of the extracted candidates of the large intestine region in the body, and the parts continuing between sets of axial cross-sectional image data. Here, the method for obtaining the large intestine region is not limited to the aforementioned method. Other known methods, such as a Region Growing method and a Level Set method, may be used.

The path setting unit 12 extracts a tree structure of the large intestine by estimating the center line of the large intestine by thinning the three-dimensional image of the large intestine region, which has been obtained as described above, and sets this tree structure, as the path of a virtual endoscope. Regarding thinning processing, a known method may be adopted. For example, methods disclosed in M. Yasue et al., "Thinning Algorithms for Three-Dimensional Gray Images and Their Application to Medical Images with Comparative Evaluation of Performance", Journal of the Institute of Electronics, Information and Communication Engineers, Vol. J79-D-II, No. 10, pp. 1664-1674, 1996 and T. Saito et al., "An Improvement of Three Dimensional Thinning Method Using a Skeleton Based on the Euclidean Distance Transformation—A Method to Control Spurious Branches —", Journal of the Institute of Electronics, Information and Communication Engineers, Vol. J84-D-II, No. 8, pp. 1628-1635, 2001, and the like may be used.

The path setting unit 12 outputs information about the path of the virtual endoscope obtained as described above to the display control unit 17. The path of the virtual endoscope is displayed on the display 3 by the display control unit 17.

The operation amount obtainment unit 13 obtains an operation amount of drag operation or wheel operation of a mouse 4a performed by a user after a predetermined point of interest has been specified by the user in the virtual endoscopic image displayed on the display 3.

The movement distance obtainment unit 14 obtains, based on the operation amount obtained by the operation amount obtainment unit 13, a distance of movement of the virtual endoscope on the path from an initial viewpoint. A method for obtaining the distance of movement will be described in detail later. Here, the initial viewpoint is a viewpoint of a virtual endoscopic image that is initially specified by the user.

The view line vector setting unit 15 sets, based on the distance of movement obtained by the movement distance obtainment unit 14, view line vectors by sequentially changing the view line vectors from an initial view line vector with its start point located at the initial viewpoint to a shortest view line vector connecting a viewpoint on the path at a shortest distance from the point of interest and the point of interest to each other by moving, along the path, a viewpoint of the virtual endoscope on the path from the initial viewpoint closer to the point of interest and by changing the direction of a view line of the virtual endoscope closer to a direction toward the point of interest.

Specifically, the view line vector setting unit 15 sequentially sets view line vectors in such a manner that the position of a viewpoint gradually becomes closer to the point of interest, and also that the direction of a view line gradually becomes closer to the front direction of the point of interest. The method for setting a view line vector will be described later in detail.

The virtual endoscopic image generation unit 16 receives a view line vector that has been set by the view line vector setting unit 15 and a three-dimensional image of the large intestine region that has been obtained by the tubular tissue region obtainment unit 11, and generates a virtual endoscopic image based on them.

Specifically, the virtual endoscopic image generation unit 16 obtains, as a virtual endoscopic image, a projection image by center projection by projecting, onto a predetermined projection plane, a three-dimensional image on plural view lines radially extending with respect to the input view line vector, as a center. As a specific center projection method, for example, a known volume rendering technique and the like may be used.

The display control unit 17 displays, on the display 3, the virtual endoscopic image generated by the virtual endoscopic image generation unit 16 and a point of interest specified by the user.

Further, the display control unit 17 receives the three-dimensional image of the large intestine region obtained by the tubular tissue region obtainment unit 11. The display control unit 17 displays a three-dimensional image of the whole large intestine by a voxel model or a surface model on the display 3 by performing volume rendering or surface rendering on the received three-dimensional image.

Further, the display control unit 17 displays the path of the virtual endoscope that has been set by the path setting unit 12 by superimposing the path of the virtual endoscope on the three-dimensional image of the whole large intestine. A user specifies the aforementioned initial viewpoint by specifying a point on this path.

The input device 4 includes a mouse 4a (corresponding to an operation unit) and a keyboard 4b. The input device 4 receives an input of operation by a user.

In the embodiment of the present invention, the position of a cursor is specified as the position of a point of interest by specification of the position of the cursor in a virtual endoscopic image by the user by using the mouse 4a and by performance of click operation of the mouse 4a by the user. In other words, the input device 4 corresponds to the point-of-interest specification receiving unit in the claims of the present application.

Further, in the embodiment of the present invention, movement of the initial viewpoint is received by receiving drag operation or wheel operation of the mouse 4a by the user. As described above, the operation amount obtainment unit 13 obtains the operation amount of drag operation or wheel operation of the mouse 4a. The movement distance obtainment unit 14 obtains, based on the operation amount, a distance of movement from the initial viewpoint.

Next, the action of the endoscopic image diagnosis support system according to an embodiment of the present invention will be described with reference to the flowchart illustrated in FIG. 2 and FIG. 3 through FIG. 6.

First, a user inputs identification information about a subject to be examined by using the keyboard 4b of the input device 4 or the like. The three-dimensional image obtainment unit 10 of the endoscopic image diagnosis support apparatus 1 obtains a three-dimensional image 5 corresponding to the received identification information about the subject to be examined by reading out the three-dimensional image 5 from the three-dimensional image storage server 2 (S10).

The three-dimensional image obtained by the three-dimensional image obtainment unit 10 is input to the tubular tissue region obtainment unit 11. The tubular tissue region obtainment unit 11 obtains the large intestine region by extracting the large intestine region based on the received three-dimensional image (S12).

The three-dimensional image of the large intestine region obtained by the tubular tissue region obtainment unit 11 is output to the display control unit 17. The display control unit 17 displays the three-dimensional image of the whole large intestine region on the display 3 (S14).

The three-dimensional image of the large intestine region obtained by the tubular tissue region obtainment unit 11 is input to the path setting unit 12. The path setting unit 12 sets the path of the virtual endoscope, as described above, by obtaining the path of the virtual endoscope based on the received three-dimensional image of the large intestine region (S16). Further, the path of the virtual endoscope obtained by the path setting unit 12 is output to the display control unit 17. The display control unit 17 displays the received path of the virtual endoscope on the display 3. At this time, the display control unit 17 displays the path of the virtual endoscope by superimposing the path on the three-dimensional image of the large intestine region.

Then, the user specifies a predetermined point on the path of the virtual endoscope, as initial viewpoint P1 (0≤P1≤L is the length of the path), by using the mouse 4a (corresponding to the initial viewpoint specification receiving unit). The coordinate value (xP1, yP1, zP1) of the initial viewpoint is output to the view line vector setting unit 15 (S18).

Figure 5:
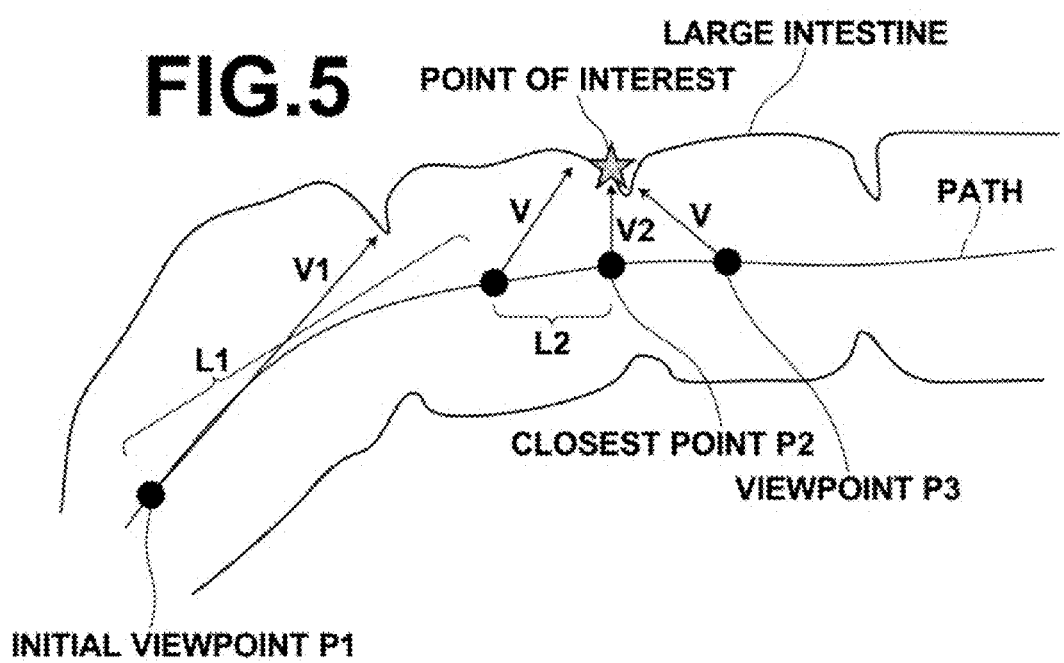
FIG. 5 is a diagram for explaining a method for setting a view line vector.

The view line vector setting unit 15 sets initial view line vector V1 based on the received coordinate value (xP1, yP1, zP1) of initial viewpoint P1 and the direction of a view line that has been initially set in advance. The view line vector setting unit 15 outputs information about initial view line vector V1 to the virtual endoscopic image generation unit 16 (S20). FIG. 5 is a diagram for explaining a method for setting a view line vector according to an embodiment of the present invention. Here, initial view line vector V1, as illustrated in FIG. 5, is set. The direction of the view line of initial view line vector V1 is not always a direction toward the point of interest, which will be specified later, but may be a position that has been initially set in advance.

Figure 3:
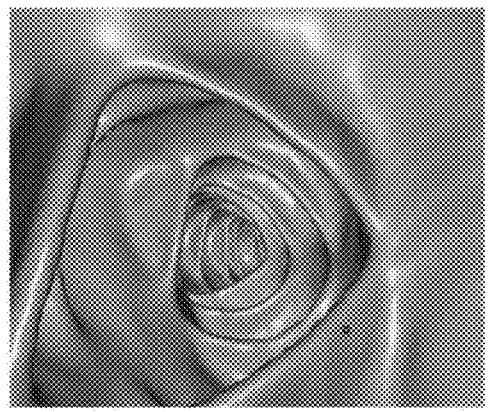
FIG. 3 is a diagram illustrating an example of a virtual endoscopic image generated based on an initial view line vector.

The virtual endoscopic image generation unit 16 generates a virtual endoscopic image based on the received information about initial view line vector V1, and outputs the virtual endoscopic image to the display control unit 17. The display control unit 17 displays the received virtual endoscopic image on the display 3 (S22). FIG. 3 illustrates an example of a virtual endoscopic image generated based on initial view line vector V1.

Figure 4:
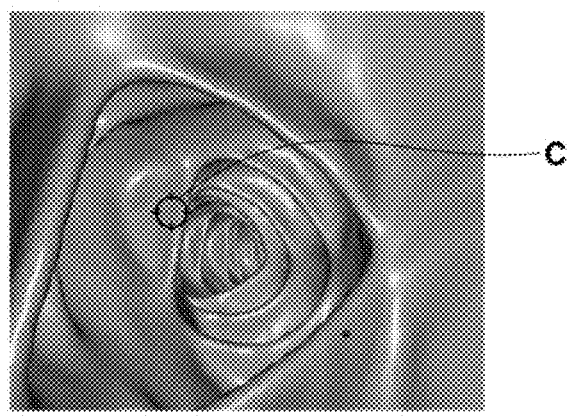
FIG. 4 is a diagram illustrating an example of a virtual endoscopic image and a cursor.

Further, as illustrated in FIG. 4, the display control unit 17 displays cursor c on the virtual endoscopic image. The position of a point of interest in the virtual endoscopic image is specified by an operation of moving cursor c to the point of interest by a user by using the mouse 4a, and by a click operation of the mouse 4a at the position of the point of interest by the user (S24). In the diagram of FIG. 6, a section at the top illustrates an example of a virtual endoscopic image when a point of interest has been specified by cursor c.

Further, position information (X, Y) about the point of interest on the display specified by the user is obtained. The position information (X, Y) is output to the view line vector setting unit 15. The view line vector setting unit 15 calculates coordinate value (x, y, z) of the point of interest in a three-dimensional image corresponding to the received position information (X, Y) on the display. Since the virtual endoscopic image is an image obtained by volume rendering, it is possible to obtain the coordinate value (x, y, z) in the three-dimensional image corresponding to coordinate value (X, Y) on the display.

Then, the view line vector setting unit 15 calculates coordinate value (xP2, yP2, zP2) of closest point P2 (0≤P2≤L, L is the length of the path), which is a viewpoint on the path at the shortest distance from the point of interest, as illustrated in FIG. 5. Further, the view line vector setting unit 15 sets shortest view line vector V2 (x-xP2, y-yP2, z-zP2) connecting the coordinate value (xP2, yP2, zP2) of this closest point P2 and the coordinate value (x, y, z) of the point of interest to each other.

Next, when the user has performed a drag operation from a state in which the point of interest was being clicked, or when the user has released a click and performed wheel operation, the operation amount obtainment unit 13 obtains the operation amount of the operation (S26). Specifically, for example, when the coordinate value of cursor c during drag operation by the mouse 4a or after drag operation by the mouse 4a is (X',Y'), operation amount d by the mouse 4a is:

$$d=\sqrt{((X'-X)^2+(Y'-Y)^2)}.$$

Then, operation amount d obtained by the operation amount obtainment unit 13 is output to the movement distance obtainment unit 14. The movement distance obtainment unit 14 obtains, based on received operation amount d, a distance of movement along the path from initial viewpoint P1 on the path (S28). Specifically, the movement distance obtainment unit 14 obtains distance L1 of movement, as illustrated in FIG. 5, by performing calculation using the following expression by using control amount C=d×a (a: constant):

$$L1=C/(P2-P1).$$

Next, distance L1 of movement obtained by the movement distance obtainment unit 14 is output to the view line vector setting unit 15. The view line setting unit 15 sets new view line vector V by performing calculation of the following expression by using the aforementioned initial view line vector V1, shortest view line vector V2 and distance L1 of movement (S30). Here, "D" in the following expression is represented by D=L2/(L1+L2), and L2 is a value obtained by subtracting distance L1 of movement from a distance on the path from initial viewpoint P1 to closest point P2, as illustrated in FIG. 5:

$$V=V1\times(1.0-D)+V2\times D.$$

The new view line vector V, which has been newly set based on the operation amount of the mouse 4a as described above, is output to the virtual endoscopic image generation unit 16. The virtual endoscopic image generation unit 16 generates a virtual endoscopic image based on the new view line vector V, and outputs the virtual endoscopic image to the display control unit 17. The display control unit 17 displays the received virtual endoscopic image based on view line vector V on the display 3. In the diagram of FIG. 6, a second section from the top illustrates an example of a virtual endoscopic image soon after starting a drag operation or a wheel operation by the mouse 4a. The virtual endoscopic image at this point of time resembles a virtual endoscopic image based on initial view line vector V1.

The view line vector setting unit 15 sequentially sets view line vectors V, based on an operation amount by the mouse 4a, by sequentially changing the view line vectors V from initial view line vector V1 to shortest view line vector V2, as described above, and outputs the view line vectors V to the virtual endoscopic image generation unit 16.

The virtual endoscopic image generation unit 16 sequentially generates virtual endoscopic images based on the received view line vectors V, and outputs the virtual endoscopic images to the display control unit 17. The display control unit 17 sequentially updates the virtual endoscopic images, and displays the virtual endoscopic images on the display 3.

Here, the expression for calculating view line vector V is not limited to the above expression. View line vector V may be calculated, for example, based on the following expression. In both of the above expression and the following expression, view line vectors are sequentially set in such a manner that the direction of a view line gradually becomes closer to a direction toward the point of interest as a viewpoint becomes closer to the point of interest by an operation by the mouse 4a. However, in the following expression, the direction of the view line is directed to the direction toward the point of interest after the viewpoint has moved to the vicinity of the point of interest to some extent. In other words, an amount of change of the view line vector becoming closer to shortest view line vector V2 when the viewpoint is present closer to closest point P2 is made larger than an amount of change when the viewpoint is present closer to initial viewpoint P1. When view line vectors are sequentially set in this manner, and virtual endoscopic images are sequentially updated and displayed, virtual endoscopic images change more smoothly, and observation of the point of interest becomes easy:

$$V=V1\times(1.0-D^2)+V2\times D^2.$$

When the position of the viewpoint has been moved to closest point P2 by a drag operation or a wheel operation by the mouse 4a, the view line vector setting unit 15 outputs shortest view line vector V2 to the virtual endoscopic image generation unit 16. The virtual endoscopic image generation unit 16 generates a virtual endoscopic image based on the received shortest view line vector V2. The virtual endoscopic image based on shortest view line vector V2 is output to the display control unit 17, and displayed on the display 3 (S32). Specifically, a virtual endoscopic image viewing the point of interest from the front direction, and in which the point of interest is positioned at the center, is displayed on the display 3 at this time. In the diagram of FIG. 6, a third section from the top illustrates an example of a virtual endoscopic image based on view line vector V when the position of a viewpoint has become close to closest point P2. Here, the point of interest is positioned at the center of a virtual endoscopic image based on shortest view line vector V2 with the viewpoint located at closest point P2.

When a drag operation or a wheel operation by the mouse 4a has been further performed, the coordinate value of viewpoint P3, which is moved further forward from closest point P2, is obtained. The view line vector setting unit 15 sets new view line vector V connecting the coordinate value of the viewpoint P3 and the coordinate value of the point of interest to each other, and outputs the view line vector V to the virtual endoscopic image generation unit 16.

The virtual endoscopic image generation unit 16 generates a virtual endoscopic image based on the received new view line vector V, and outputs the virtual endoscopic image to the display control unit 17. The display control unit 17 updates and displays the virtual endoscopic image on the display 3. Specifically, a virtual endoscopic image viewing the point of interest from the back, and in which the point of interest is positioned at the center, is displayed on the display 3 at this time (S34). In the diagram of FIG. 6, a section at the bottom illustrates an example of a virtual endoscopic image viewing the point of interest from the back, as described above.

Then, when a user has ended a drag operation by releasing a click of the mouse 4a, or when the user has input an instruction for ending a wheel operation by clicking a wheel or the like after the wheel operation, a signal indicating that the operation has ended is output to the view line vector setting unit 15 (S36).

When the view line vector setting unit 15 has received the aforementioned signal indicating that the operation has ended, the view line vector setting unit 15 changes the viewpoint of the currently set view line vector to the initial viewpoint, and sets the initial view line vector again. The view line vector setting unit 15 outputs information about the initial view line vector to the virtual endoscopic image generation unit 16.

The virtual endoscopic image generation unit 16 generates a virtual endoscopic image again based on the received initial view line vector, and outputs the virtual endoscopic image to the display control unit 17. The display control unit 17 updates and displays the virtual endoscopic image (S38). Specifically, when a drag operation or a wheel operation by the mouse 4a has ended, the first virtual endoscopic image is displayed on the display 3 again.

According to the endoscopic image diagnosis support system of the aforementioned embodiments, specification of a point of interest is received. After then, a distance of movement on a path from an initial viewpoint is obtained based on an operation amount received at the mouse 4a. View line vectors are set, based on the obtained distance of movement, by sequentially changing the view lines from the initial view line vector to the shortest view line vector by moving, along the path, a viewpoint of the virtual endoscope on the path from the initial viewpoint closer to the point of interest, and also by changing the direction of the view line closer to the direction toward the point of interest. Further, virtual endoscopic images are sequentially generated based on the set view line vectors, and the generated virtual endoscopic images are sequentially displayed. Therefore, it is possible to sequentially generate and display virtual endoscopic images of a surrounding region of the point of interest and also to generate and display a virtual endoscopic image based on the shortest view line vector, in other words, a virtual endoscopic image viewing the point of interest from the front, and which is easily observable, only by a simple operation by the mouse 4a.

In the descriptions of the above embodiments, the view line vector setting unit 15 immediately changes the currently set view line vector to the initial view line vector when a drag operation or a wheel operation by the mouse 4a has ended. However, it is not necessary that the operation is performed in this manner. For example, view line vectors may be sequentially changed and set while the viewpoint of the currently set view line vector is changed to the initial viewpoint. Further, virtual endoscopic images may be sequentially updated and displayed based on the change of the view line vectors. In other words, the virtual endoscopic images that have been sequentially updated till the virtual endoscopic image based on the currently set view line vector is displayed may be sequentially displayed in a reverse order back to the initial virtual endoscopic image.

As described above, when a drag operation or a wheel operation by the mouse 4a has ended, if a virtual endoscopic image based on the initial view line vector is generated and displayed again, it is not necessary to set a viewpoint nor the direction of a view line again when a user wants to observe virtual endoscopic images from the initial viewpoint again by changing viewpoints, or when the user wants to return to the the virtual endoscopic image that was displayed first.

Further, in the descriptions of the above embodiments, a drag operation or a wheel operation ends after the viewpoint has passed closest point P2 and moved to the position of viewpoint P3. However, it is not necessary that the operation is performed in this manner. The drag operation or the wheel operation may be ended at some point while a viewpoint is moved from initial viewpoint P1 to closest point P2. A virtual endoscopic image based on a currently set view line vector is updated to the virtual endoscopic image based on the initial view line vector and displayed, as described above, also in that case.

Further, in the endoscopic image diagnosis support system of the above embodiments, an instruction for recording a virtual endoscopic image may be received during a drag operation or a wheel operation by the mouse 4a. Further, the virtual endoscopic image generation unit 16 may record a virtual endoscopic image generated based on the view line vector that is being set at the time when the instruction for recording has been received. When a virtual endoscopic image at a desirable viewpoint is recorded in this manner, it is possible to use the virtual endoscopic image for a desirable purpose by reading out the virtual endoscopic image later to check the virtual endoscopic image again. Here, the instruction for recording the virtual endoscopic image may be input, for example, by using the "Enter" key of the keyboard 4b.

Further, in the endoscopic image diagnosis system according to the above embodiments, the user may be notified that the currently set view line vector is shortest view line vector V2. In other words, the user may be notified that the virtual endoscopic image currently displayed on the display 3 is a virtual endoscopic image viewing the point of interest from the front direction. As a method for notifying the user, for example, the display control unit 17 (corresponding to a notification unit) may display a message, a mark or the like on the display 3. Alternatively, the display control unit 17 may notify the user by voice. When the user is notified in this manner, the user can easily recognize that the currently displayed virtual endoscopic image is a virtual endoscopic image viewing the point of interest from the front direction.

Figure 7:
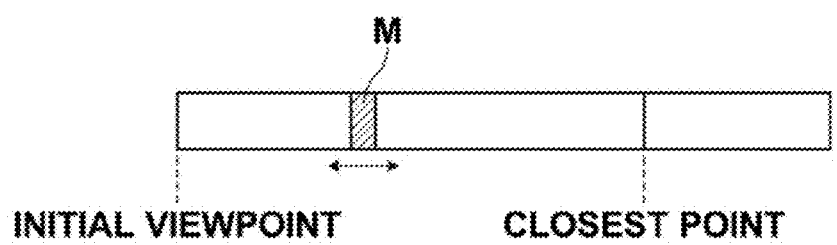
FIG. 7 is a diagram illustrating an example of marker M, which horizontally moves based on movement of the position of a viewpoint, and a scale indicating a position on a path.

Further, the user may be notified that the currently set view line vector is a view line vector including a viewpoint that has been moved further forward from closest point P2 of shortest view line vector V2. In other words, the user may be notified that the virtual endoscopic image that is currently displayed on the display 3 is a virtual endoscopic image viewing the point of interest from the back. Specifically, for example, the display control unit 17 may notify the user by displaying marker M, which horizontally moves based on movement of the position of the viewpoint, and a scale indicating a position on the path, as illustrated in FIG. 7, on the display 3, and by displaying marker M toward the right of the closest point on the scale. When the user is notified in this manner, the user can easily recognize that the currently displayed virtual endoscopic image is a virtual endoscopic image viewing the point of interest from the back.

Further, the view line vector setting unit 15 may calculate a distance between the viewpoint of the currently set view line vector and the point of interest, and the display control unit 17 may display the distance on the display 3.

What is claimed is:

1. A virtual endoscopic image display apparatus comprising:
   a memory configured to store computer-executable instructions; and
   a processor configure to execute the stored instructions, which when executed by the processor perform the following operations:
   generates, based on a three-dimensional image of a subject to be examined, a virtual endoscopic image by a virtual endoscope, simulating imaging performed by an endoscope inserted into the subject to be examined;
   displays the virtual endoscopic image;
   sets a path of the virtual endoscope in the three-dimensional image of the subject to be examined;
   receives specification of a point of interest in the virtual endoscopic image;
   obtains an operation amount after specification of the point of interest has been received;
   obtains, based on the operation amount, a distance of movement of the virtual endoscope on the path from an initial viewpoint; and
   sets, based on the distance of movement, view line vectors by sequentially changing the view line vectors from an initial view line vector with its start point located at the initial viewpoint to a shortest view line vector, which connects a viewpoint on the path at a shortest distance from the point of interest and the point of interest to each other, by moving, along the path, a viewpoint of the virtual endoscope on the path from the initial viewpoint closer to the point of interest and also by changing the direction of a view line of the virtual endoscope closer to a direction toward the point of interest,
   wherein the processor is further configured to:
   sequentially generate the virtual endoscopic image based on the view line vector,
   sequentially display the virtual endoscopic image based on change of the view line vectors,
   sequentially set the view line vectors in such a manner that the direction of a view line gradually becomes closer to a direction toward the point of interest as the viewpoint becomes closer to the point of interest, and
   employ the initial view line vector, the shortest view line vector, and the movement distance to sequentially calculate and set view line vectors corresponding to the movement distance.

2. The virtual endoscopic image display apparatus, as defined in claim 1, wherein the processor is further configured to set a view line vector connecting a viewpoint on the path moved along the path further forward from the viewpoint of the shortest view line vector and the point of interest to each other.

3. The virtual endoscopic image display apparatus, as defined in claim 1, wherein the processor is further configured to set a view line vector by changing a viewpoint of a view line vector that is currently set to the initial viewpoint when an operation at the operation unit has ended.

4. The virtual endoscopic image display apparatus, as defined in claim 3, wherein the processor is further configured to set view line vectors by sequentially changing the view line vectors from the viewpoint of the view line vector that is currently set to the initial viewpoint, and
   sequentially display the virtual endoscopic image based on change of the view line vectors.

5. The virtual endoscopic image display apparatus, as defined in claim 1, wherein the processor is further configured to receive an instruction for recording the virtual endoscopic image, and record a virtual endoscopic image generated based on a view line vector that is being set when the instruction for recording has been received.

6. The virtual endoscopic image display apparatus, as defined in claim 1 wherein the processor is further configured to make an amount of change of the view line vector becoming closer to the shortest view line vector larger when a viewpoint is present closer to the viewpoint on the path at the shortest distance from the point of interest than when the viewpoint is present closer to the initial viewpoint.

7. The virtual endoscopic image display apparatus, as defined in claim 1, wherein the processor is further configured to notify
   that the shortest view line vector is being set.

8. The virtual endoscopic image display apparatus, as defined in claim 1, wherein the processor is further configured to notify
   that notifies that a view line vector that is currently set is a view line vector including a viewpoint moved on the path further forward from the viewpoint of the shortest view line vector.

9. The virtual endoscopic image display apparatus, as defined in claim 1, wherein the processor is further configured to receive
specification of the initial viewpoint in the three-dimensional image.

10. The virtual endoscopic image display apparatus, as defined in claim 1, wherein the processor is further configured to receive specification of the point of interest by receiving specification of the position of a cursor displayed in the virtual endoscopic image and a click operation of a mouse.

11. The virtual endoscopic image display apparatus, as defined in claim 1,
further comprising a mouse, and
wherein the processor is further configured to obtain an operation amount of drag operation or wheel operation of the mouse.

12. A virtual endoscopic image display apparatus as defined in claim 1, wherein the processor is further configured to
generate virtual endoscopic images based on the view line vector set by the view line vector setting unit such that the point of interest gradually approaches the center position of the virtual endoscopic image accompanying movement of the viewpoint.

13. A virtual endoscopic image display method comprising the steps of:
generating, based on a three-dimensional image of a subject to be examined, a virtual endoscopic image by a virtual endoscope, simulating imaging performed by an endoscope inserted into the subject to be examined;
displaying the generated virtual endoscopic image;
setting a path of the virtual endoscope in the three-dimensional image of the subject to be examined;
receiving specification of a point of interest in the virtual endoscopic image;
obtaining an operation amount received at an operation unit after specification of the point of interest has been received;
obtaining, based on the obtained operation amount, a distance of movement of the virtual endoscope on the path from an initial viewpoint;
setting, based on the obtained distance of movement, view line vectors by sequentially changing the view line vectors from an initial view line vector with its start point located at the initial viewpoint to a shortest view line vector connecting a viewpoint on the path at a shortest distance from the point of interest and the point of interest to each other by moving, along the path, a viewpoint of the virtual endoscope on the path from the initial viewpoint closer to the point of interest and by changing the direction of a view line of the virtual endoscope closer to a direction toward the point of interest;
generating sequentially the virtual endoscopic image based on the set view line vector; and
displaying sequentially the generated virtual endoscopic image based on change of the view line vectors,
wherein the view line vector setting step sequentially sets the view line vectors in such a manner that the direction of a view line gradually becomes closer to a direction toward the point of interest as the viewpoint becomes closer to the point of interest, and employs the initial view line vector, the shortest view line vector, and the movement distance to sequentially calculate and set view line vectors corresponding to the movement distance.

14. A non-transitory computer-readable recording medium having stored therein a virtual endoscopic image display program that causes a computer to perform the following operations:
generates, based on a three-dimensional image of a subject to be examined, a virtual endoscopic image by a virtual endoscope, simulating imaging performed by an endoscope inserted into the subject to be examined;
displays the virtual endoscopic image;
sets a path of the virtual endoscope in the three-dimensional image of the subject to be examined;
receives specification of a point of interest in the virtual endoscopic image;
obtains an operation amount after specification of the point of interest has been received;
obtains, based on the operation amount, a distance of movement of the virtual endoscope on the path from an initial viewpoint;
sets, based on the distance of movement, view line vectors by sequentially changing the view line vectors from an initial view line vector with its start point located at the initial viewpoint to a shortest view line vector connecting a viewpoint on the path at a shortest distance from the point of interest and the point of interest to each other by moving, along the path, a viewpoint of the virtual endoscope on the path from the initial viewpoint closer to the point of interest and by changing the direction of a view line of the virtual endoscope closer to a direction toward the point of interest;
sequentially generates the virtual endoscopic image based on the view line vector;
sequentially displays the virtual endoscopic image based on change of the view line vectors;
sequentially sets the view line vectors in such a manner that the direction of a view line gradually becomes closer to a direction toward the point of interest as the viewpoint becomes closer to the point of interest; and
employs the initial view line vector, the shortest view line vector, and the movement distance to sequentially calculate and set view line vectors corresponding to the movement distance.

* * * * *